US005739023A

United States Patent [19]

Harada et al.

[11] Patent Number: 5,739,023
[45] Date of Patent: Apr. 14, 1998

[54] STABILIZED NEUTRAL METALLOPROTEASE COMPOSITION, A METHOD OF MAKING THE COMPOSITION, AND A METHOD OF TRANSPORTING THE COMPOSITION

[75] Inventors: Tsuneo Harada; Yukio Kunisawa, both of Shinanyo; Kiyotaka Oyama, Tokyo-pref., all of Japan; Johanna C. M. Smeets, Sittard, Netherlands; Shuya Takasuga, Shinanyo, Japan; Wilhelmus J. J. Van Den Tweel, Meerssen, Netherlands

[73] Assignee: Holland Sweetener Company V.o.F., Maastricht, Netherlands

[21] Appl. No.: 693,571

[22] Filed: Aug. 7, 1996

Related U.S. Application Data

[63] Continuation of Ser. No. 297,528, Aug. 26, 1994.

[30] Foreign Application Priority Data

Aug. 27, 1993 [EP] European Pat. Off. ............. 93202517

[51] Int. Cl.$^6$ .............................. C12N 9/96; C12P 21/06
[52] U.S. Cl. .............................. 435/188; 435/68.1
[58] Field of Search ................... 435/68.1, 188

[56] References Cited

U.S. PATENT DOCUMENTS

| | | | |
|---|---|---|---|
| 4,116,768 | 9/1978 | Isowa et al. | 435/68.1 |
| 4,165,311 | 8/1979 | Isowa et al. | 560/13 |
| 4,521,514 | 6/1985 | Oyama et al. | 435/68.1 |
| 4,883,900 | 11/1989 | Keller et al. | 560/41 |
| 5,304,470 | 4/1994 | Fischer et al. | 435/68.1 |

FOREIGN PATENT DOCUMENTS

| | | | |
|---|---|---|---|
| 0214550 | 8/1986 | European Pat. Off. | 435/68.1 |
| 53026393 | 3/1978 | Japan | 435/68.1 |
| 61-12298 | 1/1986 | Japan . | |
| 62-29996 | 2/1987 | Japan . | |
| 62-259597 | 11/1987 | Japan . | |
| 62-269689 | 11/1987 | Japan . | |
| 02257890 | 10/1990 | Japan | 435/68.1 |
| 8801650 | 3/1988 | WIPO . | |

OTHER PUBLICATIONS

Chang et al. (1988) *J. Parenteral Sci. Technol.*, 42(2S). "Parenteral Formulations of Proteins and Peptides: Stability and Stabilizers", pp. S3–S26.
Chemical Abstract, vol. 107, No. 19, 1987, Columbus, Ohio, US, Abstract No. 174422g & JP-A-62029996.
Patent Abstracts of Japan, vol. 012, No. 155 (C-494) 12 May 1988 & JP-A-62 269 689, Nov., 1987.
Database WPI, Week 8609, Derwent Publications Ltd., London, GB; AN 86–059600 & JP-A-61 012 298 (Daiwa Kasei KK) 20, Jan. 1986.
Chemical Abstracts, vol. 117, No. 3, 1991, Columbus, Ohio. Abstract No. 2701v & Biotechnol. Letter, 13(11), 773–8, 1991.
Chemical Abstracts, vol. 103, No. 3, 22 Jul. 1985, Columbus, Ohio, Abstract No. 21136, & Bio/Technology (1985), 3(5), 459–64.
Yang, et al., "Synthesis in Aspartame Precursor: Alpha–L–Aspartyl–L–Phenylalanine Methyl Ester In Ethyl Acetate Using Thermolysin Entrapped In Polyurethane", Biotech. and Bioeng., vol. 32, No. 5, Aug. 20, 1988, pp. 595–603.
"Kinetic Resolution of N–Protected Amino Acid Esters in Organic Solvents Catalyzed by a Stable Industrial Alkaline Protease", Biotechnology Letters vol. 13, No. 11, pp. 773–778 (1991).

*Primary Examiner*—Jon P. Weber
*Attorney, Agent, or Firm*—Cushman Darby & Cushman IP Group of Pillsbury Madison & Sutro, LLP

[57] ABSTRACT

A method for making a stabilized neutral metalloprotease enzyme composition is described in which a neutral metalloprotease and an aqueous solution are combined to obtain a solution or slurry thereof, whereby the stabilized neutral metalloprotease enzyme composition is obtained. The aqueous solution contains an N-protected amino acid, or an N-protected amino acid is added thereto. The invention also provides a stabilized neutral metalloprotease composition, and a method of transporting the stabilized neutral metalloprotease composition.

14 Claims, No Drawings

STABILIZED NEUTRAL METALLOPROTEASE COMPOSITION, A METHOD OF MAKING THE COMPOSITION, AND A METHOD OF TRANSPORTING THE COMPOSITION

This is a continuation of application Ser. No. 08/297,528, filed on Aug. 26, 1994.

FIELD OF THE INVENTION

The present invention relates to methods of using, storing and transporting a metalloproteases enzyme in stabilized form and, more precisely, to methods of using, storing and transporting such enzyme in an aqueous solution containing the enzyme. The present invention also relates to stabilized enzyme compositions.

BACKGROUND OF THE INVENTION

Proteases are utilized in various fields of food industry and detergents. Where a protease is used in an aqueous solution or a slurry, it is known that it loses its activity due to spontaneous autolysis or denaturation (pH, temperature, etc.).

Recently, a method of synthesizing a dipeptide sweetener aspartame has been developed, using a condensation reaction catalyzed by (neutral) metalloproteases such as "thermolysin" (produced by Daiwa Chemical Co.) (K. Oyama, Bioindustry, Vol. 2, No. 9, pp. 5 to 11, 1985). Thus, proteases, particularly metalloproteases, have become important as synthetases for peptides in the industrial field. However, these enzymes are not stable, when the enzyme is used or stored in an aqueous solution or slurry for a long period of time.

Metalloproteases are generally sold in the commercial market as a powder. A powdery enzyme easily forms aerosols and therefore has a safety problem, since it can cause inflammation of the throat and eyes when adhered to the mucous membranes of them. Allergenic effects may also occur. Recently, therefore, metalloprotease enzymes are handled as a liquid product or a slurry in view of the safety in handling it. However, because of the stability of the enzyme itself, such a liquid enzyme or a slurry of enzyme must he handled at a low temperature in usage, transportation and storage, which generally results in higher costs (storage at low temperature, lower activity, etc.).

Furthermore, when a metalloprotease enzyme is used for the coupling reaction between N-benzyloxy-carbonyl-L-aspartic acid (hereinafter referred to as "Z-Asp") and L- or DL-phenylalanine methyl ester (hereinafter referred to as "PM") which is a process for production of α-L-aspartyl-L-phenylalanine methyl ester (hereinafter referred to as "Aspartame" or "APM"), the aspect of decreasing active enzyme concentration is also caused by the adsorption of enzyme on crystals of the addition product N-benzyloxycarbonylaspartyl-phenylalanine methyl ester (hereinafter referred to "Z-APM.PM", e.g. as "Z-APM.DPM") besides the problem of stabilization of the enzyme.

In case a metalloprotease, such as "thermolysin" produced from *Bacillus thermoproteolyticus* Rokko is stored or used in the form of a solution or slurry thereof, it is known that the enzyme rapidly deactivates if a certain concentration of calcium ions is not present. However, in case of presence of calcium ions scaling may occur due to calcium carbonate formation in various parts of duct lines and tanks, which will often have noticeable harmful effects in practical use of an enzyme.

SUMMARY OF THE INVENTION

The object to be attained by the present invention is to provide methods of using, storing and transporting a metalloprotease or similar protease enzyme, in a stabilized form without scaling, and to provide such stabilized enzyme compositions.

Further subject matter to be attained by the present invention is to provide a method of improvement of recovering ratio which is achieved by the suppression of adsorption of enzyme on reaction product crystals (Z-APM.(D) PM).

According to the invention presence or addition of an N-protected amino acid (hereinafter referred to as "NPAA") is effective for preventing deactivation of metalloprotease enzymes especially to noticeably improve the heat stability and storage stability of the enzymes. In particular, the effect of N-benzyloxycarbonyl-amino acids (hereinafter referred to as "NZAA") has been found noticeable. In addition, according to the invention a metalloprotease enzyme may noticeably be stabilized even in the absence of excess calcium ions by the presence or addition of NPAA. The object of the present invention thus is achieved in that an N-protected amino acid is present in or added to an aqueous solution or a slurry containing the protease.

In addition, deactivation of a metalloprotease enzyme due to stirring in the presence of a slurry may also be noticeably inhibited by the presence or addition of NPAA, which is another characteristic feature.

Furthermore, according to the invention a metalloprotease enzyme may noticeably be stabilized and the recovery ratio may noticeably be improved by the presence of NPAA when such enzyme is used in the coupling reaction between Z-Asp and PM.

Specifically, the present invention advantageously can be used for storing or handling a metalloprotease solution or slurry in the presence of NPAA, or using this stabilizing effect during the enzymatic coupling of amino acids, especially in the preparation of aspartame. In accordance with the present invention, the storage stability of metal protease enzymes and the recovery ratio of metalloprotease enzymes may noticeably be improved due to a small amount of NPAA. Accordingly, decrease of the activity of these enzymes during storage is extremely small so that not only usage or storage of such enzyme for a long period of time has become possible but also the improvement of recovery ratio of metalloprotease enzymes can be achieved. This is especially economically advantageous for handling expensive enzymes.

DETAILED DESCRIPTION OF PREFERRED EMBODIMENTS

Hereafter, the present invention will be explained in detail.

The metalloprotease to be treated by the method of the present invention are not specifically confined, but thermolysin-like (neutral) proteases are especially effectively affected. As a metalloprotease, reference is made to, for example, one produced by *Bacillus proteolyticus* or *Bacillus stearothermophilus*, or one produced by expressing a gene thereof in other hosts. The enzyme solution or slurry to be used in the present invention may be a crude one containing many impurities or a purified one.

NPAA to be used as a stabilizing additive in the method of the present invention may be in the form of a salt, such as a sodium salt of NPAA or in the form of NPAA crystals.

If desired, a solution or slurry containing various NPAA's or a mixture comprising various NPAA's may also be used. Anyway, NPAA is not specifically confined. The effects caused by NPAA are not whatsoever worsened due to presence of organic substances such as other amino acids or inorganic substances therein.

The AA's in the NPAA's may be all natural L-amino acids, but also D-amino acids; the acid group of the AA's also may be in the form of an ester group, such as the benzyl ester.

As the N-protective group of NPAA, for example, benzyloxycarbonyl (Z), tertiarybutyloxycarbonyl (BOC), formyl (F), p-methoxybenzyloxycarbonyl (pMZ) are suitable. In particular, benzyloxycarbonyl-protected amino acids (ZAA's) have been found to display an extremely excellent stabilizing effect. The enzyme retention percentage in the presence of NZAA can be as high as 90% or more while that in the absence of it is about 32% under the storage condition of 50° C. for a period of 5 hours. As examples of NZAA, mentioned are N-benzyloxycarbonyl-L-aspartic acid (also referred to as Z-Asp) where the amino acid is L-aspartic acid, N-benzyloxycarbonyl-L-glutamic acid (hereinafter referred to as Z-Glu) where the amino acid is L-glutamic acid, N-benzyloxycarbonyl-L-phenylalanine (hereinafter referred to as Z-Phe) where the amino acid is phenylalanine, and N-benzyloxycarbonylglycine (hereinafter referred to as Z-Gly) where the amino acid is glycine.

In systems having no excess of calcium ions, the enzyme retention percentage was about 44% in the absence of NPAA under the storage condition of 40° C. for a period of 5 hours. In the same system, however, deactivation of a metalloprotease enzyme was noticeably inhibited by addition of NPAA. In particular, when NZAA was added to the system, almost no protease inactivation occurred. The results show that a metalloprotease enzyme solution is extremely stable during storage or can be used at room temperature or higher for a long period of time due to the presence of NPAA. Thus, the addition of NPAA is economically highly advantageous in treating and handling an expensive enzyme. In accordance with the present invention, a metalloprotease enzyme is quite stable during handling even in the absence of excess calcium ions. Therefore, the present invention is also advantageous for preventing troubles to be caused by calcium ions, such as scaling.

It may be noticed here that JP-A-6226989 mentions stabilization of alkaliproteases useful for detergents by adding a specific amount of a reversible inhibitor such as chymostatin or Z-Phe. The present inventors, however, have observed that addition of NPAA's to other protease enzymes such as papain, chymotrypsin or substilisin (all of them not being metalloproteases, which according to the state of the art can be used in enzymatic APM-synthesis, does not result in any significant stabilization of the enzyme.

Furthermore, when the metalloprotease enzyme is used for the coupling reaction between Z-Asp and PM, the lowering of the enzyme recovery may noticeable be improved very much by the presence of NPAA in an aqueous solution or slurry of an enzyme.

The molar concentration of NPAA to be present in the aqueous solution or slurry of a metalloprotease enzyme for storing and transporting the enzyme in accordance with the present invention should be more than 30 times of that of the said enzyme, preferably more than 50 times of that of the enzyme.

On the other hand, when a metalloprotease enzyme is used for the coupling reaction between Z-Asp and PM and Z-Asp is used as NPAA, the molar concentration of Z-Asp that should be present in the aqueous solution or slurry of the enzyme after the coupling reaction should be more than 500 times of that of said enzyme, and preferably more than 1000 times of that of said enzyme. In general this means that the concentration of Z-Asp should be more than 15 mmol/l, preferable more than 30 mmol/liter.

In the coupling reaction between Z-Asp and PM, the recovery ratio of enzyme was about 90% when the concentration of Z-Asp which was present in the aqueous solution or slurry of enzyme after the coupling reaction was 50 mmol/l (molar concentration 1724 times of the enzyme concentration).

On the other hand, the recovery ratio of enzyme was only about 50% when the concentration of Z-Asp which was present in the aqueous solution or slurry of enzyme after the coupling reaction was 10 mmol/l (molar concentration 345 times of the enzyme concentration).

As mentioned above, the metalloprotease enzyme may noticeably be stabilized by the presence of NPAA in an aqueous solution or a slurry of such enzyme, and the recovery ratio of such enzyme is also noticeably improved by the presence of NPAA in an aqueous solution or a slurry of enzyme when said enzyme is used for the coupling reaction between Z-Asp and PM.

Using of a metalloprotease enzyme in the coupling reaction for the production of aspartame is therefore very much improved if the molar concentration of an N-protected amino acid such as Z-Asp, is maintained at above 500 times that of the enzyme by adding an N-protected amino acid to the coupling reaction system during and/or in the final stage of the coupling reaction.

Next, the present invention will be explained in more detail by way of the following examples, which, however, are not intended to restrict the scope of the present invention.

EXAMPLE 1

5 g of powdery Thermoase (crude thermolysin, trade name by Daiwa Chemical Co.; purity about 20%) was suspended in one liter of water containing $CaCl_2 \cdot 2H_2O$ (6.8 mmol/l) (the Thermoase concentration being 0.029 mmol/liter), and Z-Asp was added thereto until a determined concentration (2.62 mmol/liter or 24.7 mmol/liter, or in other words having a molar concentration of 90 respectively 850 times the concentration of enzyme) was reached with the pH of the resulting solution being adjusted to be 5.0 by adding 1N NaOH aqueous solution. For testing the enzyme retention percentage (i.e. the active enzyme concentration), the enzyme solution was put in a separable flask having a volume of 2 liters and controlled to have a temperature of 70° C. with stirring at 240 rpm. This was sampled at regular intervals and the amount of the remaining enzyme in each sample was measured by HPLC (High Pressure Liquid Chromatography). The results obtained are shown in Table 1.

TABLE 1

| | Retention Percentage (%) of Enzyme | | |
| --- | --- | --- | --- |
| Time (hr) | No Addition | Z-Asp (2.62 mmol/liter) | Z-Asp (24.7 mmol/liter) |
| 0 | 100 | 100 | 100 |
| 1 | 68 | 91 | 91 |

TABLE 1-continued

| | Retention Percentage (%) of Enzyme | | |
|---|---|---|---|
| Time (hr) | No Addition | Z-Asp (2.62 mmol/liter) | Z-Asp (24.7 mmol/liter) |
| 2 | 53 | 86 | 87 |
| 3 | 47 | 83 | 87 |
| 4 | 39 | 80 | 83 |
| 5 | 35 | 74 | 78 |
| 7 | 31 | 73 | 74 |

As is noted from Table 1 above, the enzyme was noticeably stabilized due to addition of Z-Asp.

EXAMPLE 2

To 100 ml of water containing 0.029 mmol/liter of powdery Thermoase (crude thermolysin, trade name by Daiwa Chemical Co.; purity about 20%) and 10 mmol/liter of $CaCl_2$, were gradually added an amount of NPAA till a determined concentration (10 mmol/liter) was reached and 0.1N NaOH aqueous solution were gradually added, the pH being adjusted to be 6.0. The thus prepared enzyme solution was put in a water bath controlled to have a temperature of 70° C. The enzyme solution was then sampled at regular intervals, and the amount of the remaining enzyme in each sample was measured by HPLC. The results obtained are shown in Table 2 below.

TABLE 2

| N-Protected Amino Acid | Retention Percentage (%) of Enzyme | | |
|---|---|---|---|
| (NPAA) | 0 hr | 2 hr | 5 hr |
| No Addition | 100 | 54 | 32 |
| Z-Asp | 100 | 89 | 75 |
| Z-ASP-OBzl (*) | 100 | 101 | 92 |
| Z-Glu | 100 | 101 | 88 |
| Z-Phe | 100 | 95 | 85 |
| Z-Gly | 100 | 88 | 68 |
| BOC-Asp | 100 | 82 | 50 |
| BOC-Glu | 100 | 89 | 59 |
| BOC-Phe | 100 | 88 | 53 |
| BOC-Gly | 100 | 76 | 40 |
| BOC-Cys-SBzl (*) | 100 | 86 | 55 |
| pMZ-Asp | 100 | 78 | 42 |
| pMZ-Glu | 100 | 78 | 40 |
| F-Asp-OBzl (*) | 100 | 71 | 48 |

(*) Bzl: Benzyl Ester

As is noted from Table 2 above, the enzyme was noticeably stabilized due to addition of NPAA, especially NZAA (Z-Asp, Z-Asp-OBzl, Z-Glu, Z-Phe and Z-Gly).

EXAMPLE 3

5 g of powdery Thermoase was dissolved in one liter of water containing $CaCl_2\text{-}2H_2O$ ($CaCl_2$ concentration=0.6 mmol/liter) or of water containing Z-Asp (Z-Asp concentration=30 mmol/liter), each with a Thermoase concentration of being 0.029 mmol/liter, and the pH of the resulting solutions was adjusted to be 6.0 with 1N NaOH aqueous solution. The enzyme solution was put in a separable flask having a volume of 2.0 liters and controlled to have a temperature of 40° C. with stirring at 200 rpm.

This was sampled at regular intervals and the amount of the remaining enzyme in each sample was measured by HPLC. The results obtained are shown in Table 3.

TABLE 3

| | Retention Percentage (%) of Enzyme | | |
|---|---|---|---|
| Time (hr) | Water | Aqueous $CaCl_2$ Solution | Z-Asp |
| 0 | 100 | 100 | 100 |
| 0.5 | 84 | 100 | 106 |
| 1 | 73 | 104 | 105 |
| 2 | 63 | 102 | 101 |
| 3 | 57 | 104 | 104 |
| 4 | 52 | 101 | 104 |
| 5 | — | 97 | 104 |
| 6 | 47 | 98 | 101 |

The experiments of table 3 show that addition of Z-Asp is as effective as the use of 0.6 mmol/liter $CaCl_2$ solution; without such excess of $Ca^{2+}$ less scaling will occur.

As is noted from Table 3 above, the enzyme was noticeably stabilized due to addition of Z-Asp, which is one of NZAA, even in the absence of excess calcium ions.

EXAMPLE 4

An amount of NPAA was added to 100 ml of an aqueous solution containing 0.029 mmol/liter of powdery Thermoase (not containing excess Ca) until a determined concentration (10 mmol/liter) was reached, in the same manner as in Example 2, the pH of the system being adjusted to be 6. This was put in a water bath controlled to have a temperature at 40° C.

The enzyme solutions were sampled at regular intervals, and the amount of the remaining enzyme was measured by HPLC. The results obtained are shown in Table 4 below.

TABLE 4

| N-Protected Amino Acid | Retention Percentage (%) of Enzyme | | |
|---|---|---|---|
| (NPAA) | 0 hr | 2 hr | 5 hr |
| No Addition | 100 | 54 | 44 |
| Z-Asp | 100 | 97 | 95 |
| Z-Asp-OBzl (*) | 100 | 94 | 98 |
| Z-Glu | 100 | 101 | 104 |
| Z-Phe | 100 | 98 | 103 |
| Z-Gly | 100 | 88 | 89 |
| BOC-Asp | 100 | 63 | 50 |
| BOC-Glu | 100 | 89 | 70 |
| BOC-Phe | 100 | 92 | 83 |
| BOC-Gly | 100 | 89 | 74 |
| BOC-Cys-SBzl (*) | 100 | 93 | 79 |
| pMZ-Asp | 100 | 77 | 60 |
| pMZ-Glu | 100 | 89 | 70 |
| F-Asp-OBzl (*) | 100 | 74 | 38 |

(*) Bzl: Benzyl Ester

As is noted from Table 4 above, the enzyme was noticeably stabilized due to addition of NPAA, especially NZAA (Z-Asp, Z-Asp-OBzl, Z-Glu, Z-phe and Z-Gly).

EXAMPLE 5

5 g of powdery Thermoase (purity=about 20%) was suspended in 750 g of water containing 0.1% $CaCl_2.2H_2O$ in separable flask having a volume of 2 liters, and 250 g of Celite (produced by Johns Manvill Corp., Grade: Standard Super-Cel) was added thereto to form a uniform slurry. This was controlled to have a temperature of 40° C., the Thermoase concentration being 0.029 mmol/liter.

Z-Asp was added to this until a determined concentration (30 mmol/liter) was reached, which was then adjusted to have pH of 7.3 with 1N aqueous NaOH solution. This was stirred with a stirrer equipped with motor at a rate of 240 rpm and was sampled at regular intervals. The retention percentage of enzyme in each sample was measured by HPLC. The results obtained are shown in Table 5 below.

TABLE 5

| | Retention Percentage (%) of Enzyme | |
|---|---|---|
| Time | No Addition of Z-Asp | Z-Asp (30 mmol/liter) |
| 0 | 100 | 100 |
| 1 | 85 | 95 |
| 3 | 70 | 88 |
| 5 | 60 | 85 |
| 7 | 55 | 79 |

As is noted from Table 5 above, the enzyme which is influenced and deactivated in the slurry was noticeably stabilized by addition of Z-Asp.

EXAMPLE 6

5 g of powdery Protease TD (product by Amano Pharmaceutical Co.; metalloprotease produced by *Bacillus stearothermophilus*; purity=about 20%) was suspended in one liter of water containing 0.1% $CaCl_2 \cdot 2H_2O$, with the concentration of Protease TD being 0.029 mmol/liter. Z-Asp was added to this until a determined concentration (10 mmol/liter) was reached, which was then adjusted to have pH of 5.0 with 1N aqueous NaOH solution. The resulting solution was put in a separable flask having a volume of 2 liters and controlled to have a temperature of 70° C. with stirring at 240 rpm. This was sampled at determined intervals, and the amount of the remaining enzyme in each sample was measured by HPLC. The results obtained are shown in Table 6 below.

TABLE 6

| | Retention Percentage (%) of Enzyme | |
|---|---|---|
| Time (hr) | No Addition of Z-Asp | Z-Asp (10 mmol/liter) |
| 0 | 100 | 100 |
| 1 | 84.5 | 97.4 |
| 2 | 71.9 | 95.5 |
| 3 | 62.9 | 93.6 |
| 4 | 53.4 | 91.6 |
| 5 | 45.5 | 92.1 |
| 7 | 36.0 | 86.6 |

As is noted from Table 6 above, the enzyme was noticeably stabilized due to addition of Z-Asp.

EXAMPLE 7

943 g of Z-Asp aqueous solution (the amount of Z-Asp was 1.0 mol) and 1258 g of DL-PM aqueous solution (the amount of PM was 2.0 mol) was mixed, warmed to 40° C., and the aqueous solution was prepared by the adjustment of pH of this solution using 25% NaOH solution, and this solution was used as the substrate solution.

Separately 1.28 g of $CaCl_2 \cdot 2H_2O$ and 127 g of NaCl was dissolved in 1242 g of purified water, and 45 g of thermoase was dissolved in this aqueous solution, and this aqueous solution was used as the aqueous solution of an enzyme.

The substrate solution and the aqueous solution were mixed in the separable-flask of 5 liters which was settled in a water-bath maintained at 40° C., and pH of this mixed solution was adjusted to be 6.0 and the coupling reaction between Z-Asp and PM was started.

The concentration of thermoase was 0.029 mmol/l as in the previous examples.

The stirring of the mixed solution was carried out with stirring speed of 130 rpm till 3.5 hours after the start of the coupling reaction, and was carried out with stirring speed of 30 rpm during 3.5 hours to 7 hours.

The yield of Z-APM.(D)PM based on the starting amount of Z-Asp was 80.5% after 7 hours, and the concentration of Z-Asp which remained after the coupling reaction was 55.9 mmol/l.

The thermoase which were recovered after the coupling reaction was 41.4 g and the recovery ratio was about 92%.

COMPARATIVE EXAMPLE 1

943 g of Z-Asp aqueous solution (the amount of Z-Asp was 1.0 mol) and 1572 g of DL-PM aqueous solution (the amount of PM was 2.5 mol) was mixed, warmed to 40° C., and the aqueous solution was prepared by the adjustment of pH of this solution using 25% NaOH solution, and this solution was used as the substrate solution.

Separately 1.28 g of $CaCl_2 \cdot 2H_2O$ and 127 g of NaCl was dissolved in 1242 g of purified water, and 45 g of thermoase was dissolved in this aqueous solution, and this aqueous solution was used as the aqueous solution of an enzyme.

In this Comparative Example the higher amount of PM as compared with Example 7 results in a lower amount of Z-Asp remaining after the coupling. It can be seen that this results in a significantly decreased thermoase recovery ratio.

The substrate solution and the aqueous solution were mixed in the separable-flask of 5 liters which was set in the water-bath maintained at 40° C., and pH of this mixed solution was adjusted to be 6.0 and the coupling reaction between Z-Asp and PM was started.

The stirring of the mixed solution was carried out with stirring speed of 130 rpm till 3.5 hours after the start of the coupling reaction, and was carried out with stirring speed of 30 rpm during 3.5 hours to 7 hours.

The yield of Z-APM.(D)PM based on the starting amount of Z-Asp was 95.2% after 7 hours, and the concentration of Z-Asp which remained after the coupling reaction was 10.5 mmol/l.

The thermoase which were recovered after the coupling reaction was 19.5 g, and the recovery ratio was about 44%.

We claim:

1. A method for preparing and storing a stabilized thermolysin which is storable without scaling which comprises: adding thermolysin to an aqueous solution to obtain a solution or slurry thereof, wherein said aqueous solution contains an N-protected amino acid, or an N-protected amino acid is added to said solution or slurry, whereby said stabilized thermolysin is obtained; and storing said stabilized thermolysin.

2. A stabilized thermolysin composition having enhanced storage stability comprising:

thermolysin;

an aqueous medium; and an N-protected amino acid.

3. A method of making a storage stabilized neutral metalloprotease enzyme composition and transporting said storage stabilized neutral metalloprotease enzyme composition to a location of use comprising the steps of:

combining a neutral metalloprotease enzyme and an aqueous solution to obtain a solution or slurry thereof, wherein said aqueous solution contains an N-protected amino acid or soluble salt thereof or an N-protected amino acid or salt thereof is added to said solution or slurry, whereby said storage stabilized neutral metalloprotease enzyme composition is obtained; and transporting said storage stabilized neutral metalloprotease enzyme composition to said location of use.

4. A method according to claim 3, wherein said N-protected amino acid is added to said solution or said slurry.

5. A method according to claim 3, wherein a salt of an N-protected amino acid is used when said stabilized neutral metalloprotease enzyme composition is being obtained.

6. A method according to claim 3, wherein said aqueous solution contains an N-protected amino acid or a soluble salt thereof.

7. A method according to claim 6, wherein the neutral metalloprotease is thermolysin.

8. A method according to claim 3, wherein the neutral metalloprotease is thermolysin or another neutral metalloprotease which catalyzes the coupling reaction between N-benzyloxycarbonyl-L-aspartic acid and L- or DL-phenylalanine methyl ester.

9. A method according to claim 3, wherein the neutral metalloprotease is a metalloprotease from *B. proteolyticus, B. thermoproteolyticus,* or *B. stearothermophilus.*

10. A method according to claim 3, 4, 5, 6, 8, 9, or 7 wherein said N-protected amino acid is an N-benzyloxycarbonylamino acid.

11. A method according to claim 3, wherein the molar concentration of said N-protected amino acid is more than 30 times the molar concentration of said enzyme.

12. A method according to claim 3, wherein the molar concentration of said N-protected amino acid is 90 or more times the molar concentration of said enzyme.

13. A method according to claim 3, wherein said stabilized neutral metalloprotease enzyme composition is obtained in the absence of scaling amounts of calcium ions.

14. A method according to claim 3, wherein said method further comprises a step of storing said stabilized neutral metalloprotease enzyme composition.

* * * * *